(12) United States Patent
Yoneyama

(10) Patent No.: US 7,113,564 B2
(45) Date of Patent: Sep. 26, 2006

(54) X-RAY IMAGING APPARATUS AND METHOD WITH AN X-RAY INTERFEROMETER

(75) Inventor: Akio Yoneyama, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/929,781

(22) Filed: Aug. 31, 2004

(65) Prior Publication Data

US 2005/0117699 A1    Jun. 2, 2005

(30) Foreign Application Priority Data

Nov. 28, 2003   (JP)   ............... 2003-398781

(51) Int. Cl.
*G21K 1/06*   (2006.01)
(52) U.S. Cl. ....................................... 378/36
(58) Field of Classification Search ................. 378/36
See application file for complete search history.

(56) References Cited

U.S. PATENT DOCUMENTS 5,173,928 A * 12/1992 Momose et al. ............ 378/4

FOREIGN PATENT DOCUMENTS

| JP | 4-348262 | 12/1992 |
|---|---|---|
| JP | 07-209212 | 1/1994 |
| JP | 10-248833 | 9/1998 |
| JP | 2002139459 A * | 5/2002 |
| JP | 2003-90807 | 3/2003 |

OTHER PUBLICATIONS

Bouse, U. et al., "An X-Ray Interferometer", Applied Physics Letter, vol. 6, No. 8 (Apr. 15, 1965) pp. 155-156.
Becker, P. et al., "The Skew-Symmetric Two-Crystal X-ray Interferometer", J. of Appl. Crystallography, vol. 7, Part 6 (Dec. 1974), pp. 593-598.

* cited by examiner

*Primary Examiner*—Edward J. Glick
*Assistant Examiner*—Chih-Cheng Glen Kao
(74) *Attorney, Agent, or Firm*—Reed Smith LLP; Stanley P. Fisher, Esq.; Juan Carlos A. Marquez, Esq.

(57) ABSTRACT

An imaging apparatus and methods for using the same based upon the interposing of a sample in an X-ray interferometer, such as a Bonse-Hart interferometer. An incident X-ray is split, reflected and combined to form first and second interference beams. When a sample is placed in an optical path of one of the beams, the X-ray intensity, phase and transmission direction of the X-ray beam are altered. A change in the amplitude and phase of the interference beams caused by the sample are obtained using a fringe scanning method, and a detector is used to detect the resulting image.

19 Claims, 11 Drawing Sheets

X-ray

X-ray

X-RAY IMAGING APPARATUS AND METHOD WITH AN X-RAY INTERFEROMETER

CLAIM OF PRIORITY

The present application claims priority from Japanese application JP 2003-398781 filed on Nov. 28, 2003, the content of which is hereby incorporated by reference into this application.

FIELD OF THE INVENTION

The present invention relates generally to an X-ray imaging apparatus and an X-ray imaging method, and more particularly to an apparatus and a method for nondestructively inspecting the inside of an object.

BACKGROUND OF THE INVENTION

As an imaging apparatus for nondestructively observing the inside of a sample by using X-rays, there are an absorption contrast X-ray imaging apparatus using changes in an intensity caused by a sample as contrast, and a phase contrast X-ray imaging apparatus using phase-shift caused by a sample as contrast. The former absorption contrast X-ray imaging apparatus mainly comprises an X-ray source, a sample positioning mechanism and a detector. The X-rays emitted from the X-ray source are irradiated on a sample positioned by the sample positioning mechanism, and detected by the detector after passing through the sample. Thus an image constituting the changes in the intensity caused by absorption of the sample as contrast was obtained. Since a measuring principle and a structure of the apparatus are relatively simple, this imaging technique is widely used in many fields including a medical diagnostic field. In the case of two dimensional observation, it is called roentgen, and in the case of three dimensional observation by a Computed Tomography (CT) scanner, it was called X-ray CT.

On the other hand, there are an apparatus described in the Non-Patent Document 1 (Appl. Phys. Lett. 6, 155 (1965)), an apparatus disclosed in the Patent Publication Document 1 (JP-A-10-248833) and the like as the latter phase contrast X-ray imaging apparatus. In general, the phase-shift caused by a sample is remarkable large as compared with changes in the intensity, so the phase contrast X-ray imaging apparatus has an advantage in that the sensitivity is higher than that of the absorption contrast X-ray imaging apparatus. For this reason, even if an imaging target is biological soft tissue composed mainly of light elements such as oxygen and carbon, which have been difficult to observe by the absorption contrast X-ray imaging apparatus, the phase contrast X-ray imaging apparatus makes it possible to observe the inside structure of it with low X-ray exposures and without using contrast agents nondestructively and in a state of high-sensitivity.

The phase contrast X-ray imaging apparatus as described above is constituted by adding an X-ray interferometer such as a Bonse-Hart interferometer (described in Non-Patent Document 1 (Appl. Phys. Lett. 6, 155 (1965)), or an interferometer (described in Non-Patent Document 2 (J. Appl. Cryst. 7, 593 (1974)) which is composed by two crystal blocks, to an X-ray source, a sample positioning mechanism and a detector. The Bonse-Hart interferometer, as shown in FIG. 1, has three wafers (beam splitter 1, mirror 2 and analyzer 3) arranged in parallel and at equal intervals on a crystal block fabricated from a perfect crystal ingot. An incident X-ray 4 is split into two beams such as a beam 5 and a beam 6 by the beam splitter 1, the beams are reflected by the mirror 2 and are combined on the analyzer 3 to form two interference beams 7 and 8. When a sample 9 is positioned in an optical path of the beam 5 or the beam 6, the phase shift caused by the sample 9 appears as the changes in the intensities of interference beams 7 and 8 by the principle of superposition (interference pattern). The phase map (spatial distribution of phase-shift caused by the sample) was calculated from the interference patterns detected by an image detector.

Furthermore, an imaging apparatus enabling the three dimensional nondestructive observation by combining the phase contrast imaging method and the method for normal X-ray CT, is disclosed in Patent Publication Document 2 (JP-A-4-348262) etc. In this case, the X-ray is irradiated on the sample from a plurality of directions different from each other in the same way as that of the normal X-ray CT, and a cross sectional image of the sample is reconstructed from the phase contrast projection images obtained for respective projections.

The X-ray is approximately transparent for the light elements such as oxygen and carbon, and almost all of incident X-rays are passed through the object. Therefore, the change in the intensity caused by absorption of a sample is extremely small, and it is difficult to perform the fine observations of a sample mainly composed by the light elements such as biological soft tissues and organic material etc. by the absorption contrast X-ray imaging apparatus. In order to improve the sensitivity, the contrast agents and/or an extension of exposure time is tried to be used. However, in this case, some problems that a position can be observed is limited and/or an X-ray exposure is increased, has been occurred.

On the other hand, though the sensitivity of the phase contrast X-ray imaging method is satisfactorily sufficient, the phase-shift $\alpha$ generated by the sample is detected as a wrapped value $\alpha'$ ($\alpha'=\alpha-\mathrm{Int}(\alpha/2\pi)*2\pi$) in its region of $0-2\pi$, as shown in FIG. 2. Therefore, a complicated calculation called a phase unwrapping method (described in JP-A-2001-153797) is required to obtain the true phase-shift $\alpha$. Furthermore, in a region where a shape and an internal structure of the sample is complicated and its density is rapidly varies spatially, an optical path deviates from an original optical path by X-ray diffraction, the visibility of an interference pattern is lowered or an interference fringes are disappeared. As a result, the unwrapping processing cannot be performed normally and the phase-shift $\alpha$ cannot be obtained accurately. To avoid this problem, a method that the sample is placed in a sample cell filled liquid to reduce a difference of density between the sample and its periphery, is disclosed in JP-A-7-209212. An influence of the shape of the sample can be reduced by this method, but, the influence of the rapid change in the density inside the sample is not avoidable.

As evident from the above description, a sensitivity range of conventional absorption X-ray imaging and a sensitivity range of the phase contrast X-ray imaging are separated into both ends as shown in FIG. 3. For the sample including an organ of large density change such as the bone or the lung and an organ of small density change such as biological soft tissue, neither of the imaging methods can observe the sample with satisfactory sensitivity.

SUMMARY OF THE INVENTION

The purpose of the present invention is to provide an imaging apparatus and imaging method having a wide sensitivity range as shown FIG. 3, and enabling observations of a sample including an organ of large density change such as the bone or the lung and an organ of small density change such as biological soft tissue.

FIG. 4 shows a functional diagram of general X-ray interferometer. As shown in FIG. 4, an incident X-ray beam 14 is split into a first beam 15 and a second beam 16. These beams are reflected by a mirror optical system 12 respectively, and combined by an analyzer 13 to form an interference beam 17.

The intensity I of the interference beam 17 is given by Equation (1), $$I = I_1 + I_2 + 2r\sqrt{I_1 I_2} \cdot \cos(\phi) \quad (1)$$

where $I_1$ is the intensities of the beam 15, $I_2$ is the intensities of beam 16, r is a degree of coherence, $\phi$ is a phase difference between the beam 15 and 16.

The r is given by Equation (2), $$r = \frac{2J(v)}{v} \quad (2)$$

$$v = 2\pi \frac{W \Delta x}{\lambda} \quad (3)$$

where $\lambda$ is a wavelength of an incident X-ray beam, W is a divergence angle of the incident X-ray, $\Delta x$ is deviation distance between the beam 15 and 16 on the analyzer 13, and J is Bessel function of the first kind.

If the X-ray interferometer is fabricated as designed, the optical paths of the beam 15 and 16 on the analyzer 13 are completely coincident with each other ($\Delta x = 0$), and r becomes 1. On the other hand, if the X-ray interferometer has deformation of crystal block, the optical paths of the beam 15 and 16 deviate from each other on the analyzer 13 ($\Delta x \neq 0$), and r is reduced with increasing of $\Delta x$. Hereinafter, in order to simplify the calculation, it is assumed that $\Delta x = 0$.

A sample 18 which generates the change in the intensity $\Delta I$, phase-shift $\Delta p$, and the change in the direction of the X-ray $\Delta \theta$, is placed in an optical path of the first beam 15 as shown FIG. 4, the Equation (1) becomes Equation (4), $$I' = (I_1 - \Delta I) + I_2 + 2r'\sqrt{(I_1 - \Delta I) \cdot I_2} \cdot \cos(\phi + \Delta p) \quad (4)$$

where r' is a changed degree of coherence caused by $\Delta \theta$.

Assuming that a distance between the sample 18 and the analyzer 13 is R, the deviation distance $\Delta x'$ is given by Equation (5).

$$\Delta x' = R \Delta \theta \quad (5)$$

Accordingly, r' is expressed by Equation (6) as a function of $\Delta \theta$ from Equation (2) and Equation (3), $$r' = \frac{2J(kWR\Delta\theta)}{kWR\Delta\theta} \quad (6)$$

where $k = 2\pi \frac{1}{\lambda}$.

Since the $\Delta \theta$ is given by spatial phase-shift incline of the sample (see FIG. 5), $$\Delta \theta = \frac{\Delta p}{\Delta s} \quad (7)$$

Equation (6) can be expressed by $$r' = \frac{2J\left(WR\frac{\Delta p}{\Delta s}\right)}{WR\frac{\Delta p}{\Delta s}}. \quad (8)$$

Furthermore, Equation (8) can be approximated as a linear function in a range $0 < WR\Delta p/\Delta s < 1$ as shown in Equation (9). Eventually, it can be considered that r' is approximately proportional to the spatial phase-shift incline of the sample ($\Delta p/\Delta s$).

$$r' = 1 - \frac{WR\Delta p}{3.8\Delta s} \quad (9)$$

Next, the sensitivity of the imaging method according to the present invention and the conventional imaging methods are compared using the above equations. A sample having a cross sectional shape as shown in FIG. 5 (a thickness varies linearly from $t_1$ to $t_2$ with a width $\Delta s$ at a central portion) and uniform density is used for this comparison. Using the complex refractive index n of the sample $$n = 1 - \delta + i\beta \quad (10),$$

a relative intensity difference $\Delta I$ between $I_A$ and $I_B$ which passed through a region A and a region B respectively, is given by $$\frac{I_A - I_B}{I} = \frac{\Delta I}{I} = 4\pi(t_1 - t_2)\frac{\beta}{\lambda} \quad (11)$$

On the other hand, a phase-shift difference $\Delta p$ (=pA−pB) is expressed by Equation (12).

$$pA - pB = \Delta p = 2\pi(t_1 - t_2)\frac{\delta}{\lambda} \quad (12)$$

Using Equation (12), the spatial phase-shift incline ($\Delta p/\Delta s$) at a boundary of the region A and the region B is expressed by Equation (13).

$$\frac{\Delta p}{\Delta s} = 2\pi(t_1 - t_2)\frac{\delta}{\lambda} \quad (13)$$

Therefore, a relative change $\Delta A$ of an amplitude A (=2r $(I_1 \cdot I_2)^{1/2}$) of the interference beam is given by Equation (14) from Equation (1) and Equation (9) with assuming $I_A \approx I_B$.

$$\frac{\Delta A}{A} = 2\pi(t_1 - t_2)\delta\frac{WR}{\lambda\Delta s} \quad (14)$$

The ΔA is proportional to the spatial phase-shift incline (Δp/Δs) and becomes 0 excepting the boundary regions, so that ΔA cannot be simply compared with ΔI/I and Δp. Accordingly, the sensitivities of the respective imaging methods are compared by a relative signal amount at the boundary region. From Equation (12) and Equation (14), a ratio of the sensitivity of the phase contrast X-ray imaging method and the present invention is expressed by Equation (15).

$$\Delta p: \frac{\Delta A}{A} = 1: \frac{WR}{\Delta s} \quad (15)$$

From Equation (11) and Equation (14), the ratio of the sensitivity of the imaging method according to the present invention and the absorption contrast X-ray imaging method is expressed by Equation (16).

$$\frac{\Delta A}{A}: \frac{\Delta I}{I} = \frac{\delta \cdot WR}{\Delta s}: 2\beta \quad (16)$$

In an imaging using the X-ray interferometer made of a perfect silicon crystal, the divergence angle W of the incident X-ray is about the width ($W \approx 10^5$) of Bragg diffraction of the crystal, and the distance R between the sample and the analyzer is approximately 10 cm. Furthermore, the minimum value of detectable Δs is determined approximately by spatial resolution of the imaging detector ($\sim 10^{-6}$ m). Thus Δp>ΔA/A is obtained from Equation (15). In addition, since α<<β for the light elements, ΔA/A>ΔI/I is obtained from Equation (16).

To sum up the above consideration, the sensitivity range of the imaging method using the change in the amplitude ΔA/A as contrast (the present invention) can be drawn at the middle between the phase contrast X-ray imaging method and the absorption contrast X-ray imaging method as shown in FIG. 3.

Moreover, the amplitude A of the interference beam is proportional to the intensity I of the interference beam (Equation (1) and Equation (4)), and therefore A can be directly calculated from 1 without executing special operational calculation such as unwrapping processing. Accordingly, the imaging method using the change of amplitude ΔA/A as the contrast (the present invention) can cover widely the sensitivity range of the absorption contrast X-ray imaging method. Furthermore, Δp and ΔA/A are measured simultaneously by a Fourier transformation method or a fringe scanning method. As a result, by combining Δp and ΔA/A, all of the sensitivity range can be covered as shown in FIG. 3.

As explained above, aforementioned problem has been solved by the imaging apparatus and imaging method using the amount of change in the amplitude as the contrast, and/or the amount composed of the amount of change in the amplitude and the amount of phase-shift as the contrast.

DESCRIPTION OF THE PREFERRED EMBODIMENT

Figure 1:
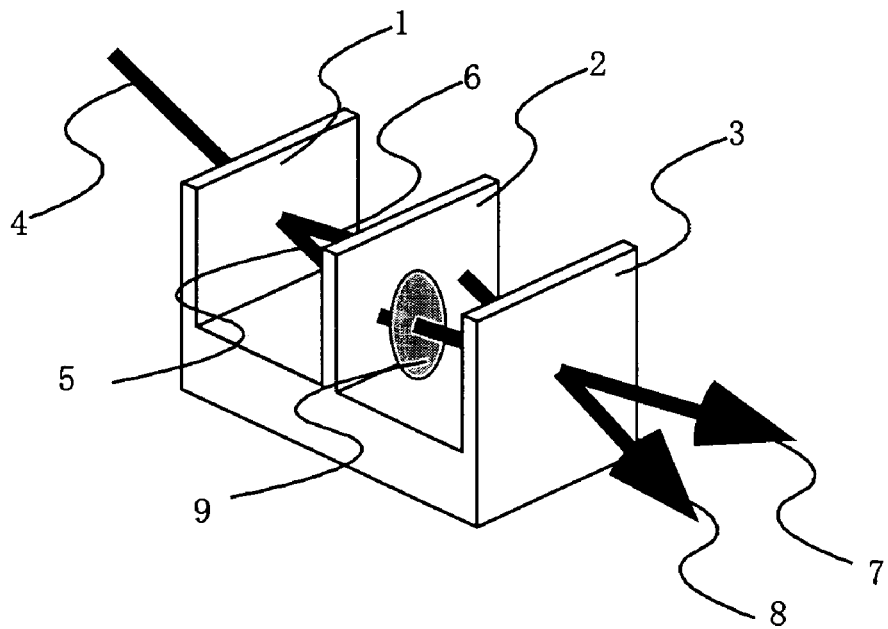
FIG. 1 is a view showing a configuration of a Bonse-Hart interferometer.
Figure 2:
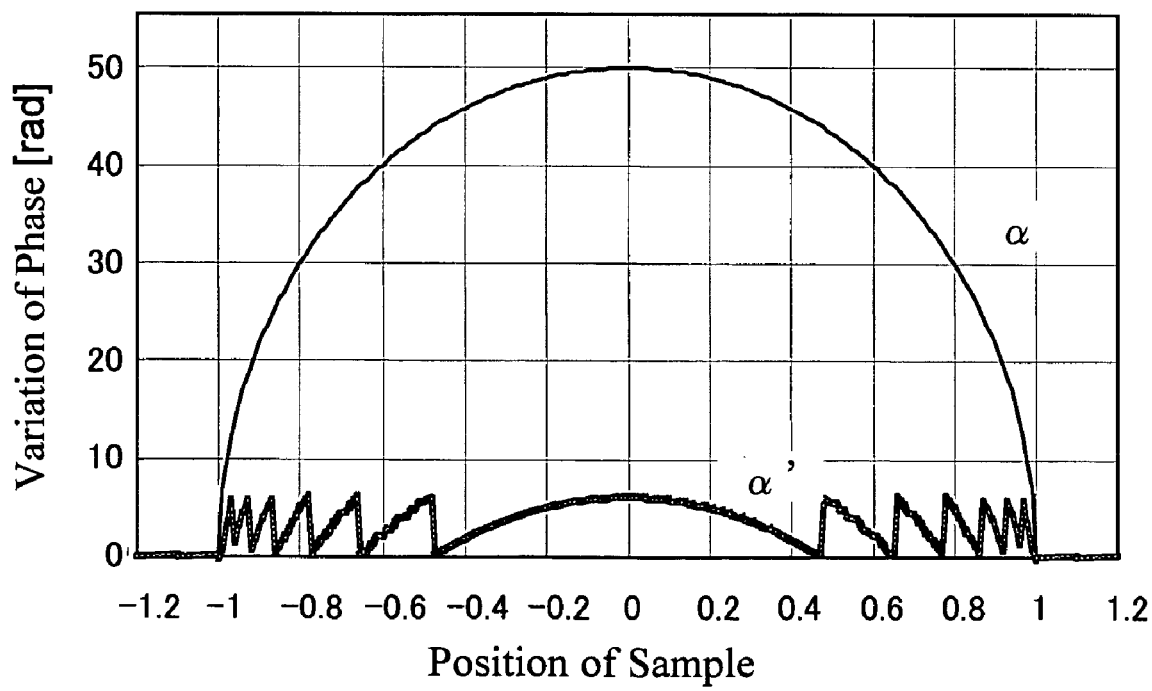
FIG. 2 is a view showing a wrapped phase α' and an unwrapped phase α.

Hereinafter, embodiments of the present invention will be described with reference to the drawings. In the drawings, elements having the same function identified by the same reference designation.

First Embodiment

Figure 6:
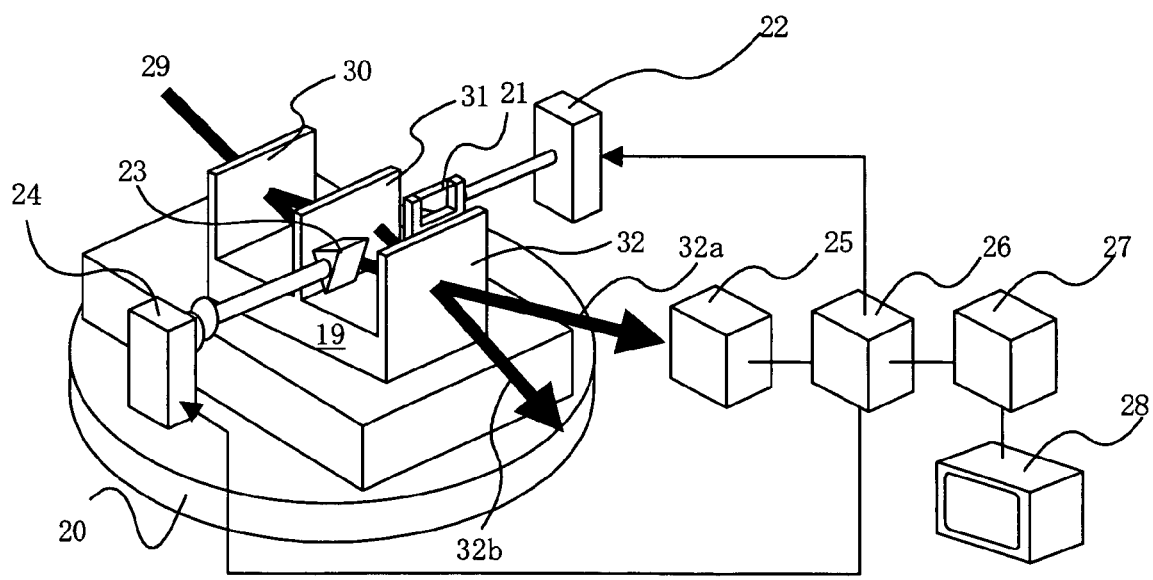
FIG. 6 is a view showing a configuration example of an X-ray imaging apparatus using a Bonse-Hart interferometer.

FIG. 6 is a view showing a constitution of one example of an X-ray imaging apparatus used in the present invention. The present X-ray imaging apparatus comprises an X-ray interferometer 19, a position adjusting mechanism 20 for an X-ray interferometer, a sample holder 21, a sample holder positioning mechanism 22, a phase shifter 23, a phase shifter positioning mechanism 24, an X-ray detector 25, a controller 26, a processing portion 27 and a display unit 28.

In this embodiment, a Bonse-Hart interferometer shown in FIG. 1 is used as the interferometer 19. An incident X-ray 29 is split, reflected and combined sequentially by a splitter 30, a mirror 31, and an analyzer 32, to from a first interference beam 32a and a second interference beam 32b in this interferometer. When a sample is placed in an optical path of split one beam by using a sample holder 21 positioned by a sample holder positioning mechanism 22, X-ray intensity, phase and a transmission direction of an X-ray are changed by the sample. As a result, the intensity of the interference beams 32a and 32b are changed, a change in an amplitude and a phase caused by the sample can be obtained by means of a fringe scanning method shown below. If a two dimensional X-ray detector is used as the X-ray detector 25, the above described change can be detected as a two dimensional image.

Figure 7:
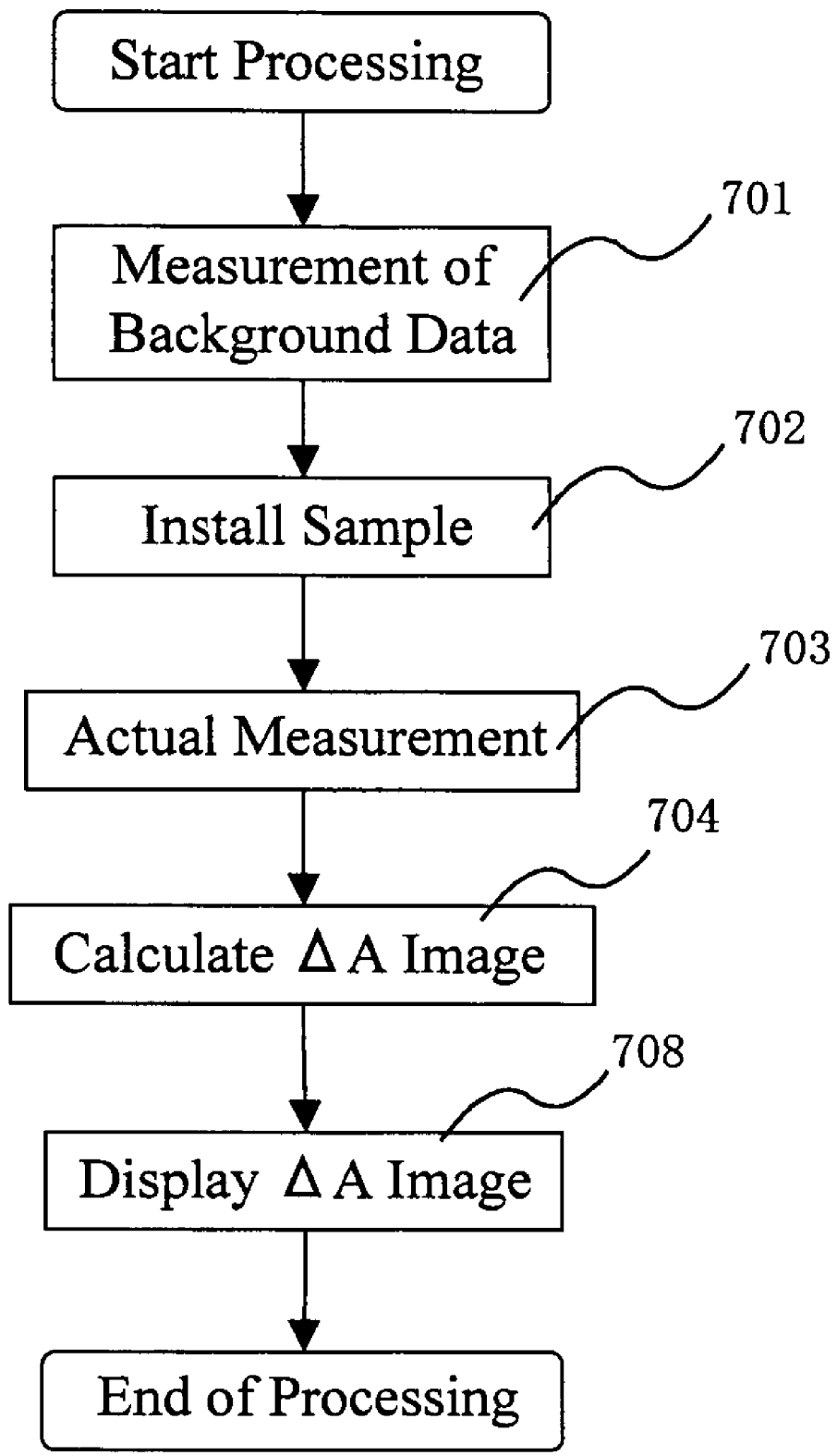
FIG. 7 is a view showing a procedure of measurement according to the embodiment 1 of the present invention.

In the embodiment 1, measurement is carried out according to a flow shown in FIG. 7. In order to exclude a background distribution (a spatial distribution with no sample) of the amplitude and the phase caused by a crystal distortion etc. of the X-ray interferometer 19, an image is obtained by measuring according to the following procedure.

(1) Before placing a sample, a background distribution of an amplitude ($A_0$) and a phase ($\Delta p_0$) are obtained by using the fringe scanning method (step 701—measurement of background data).

(2) The sample is placed in the optical path by using the sample holder 21 and the sample holder positioning mechanism 22 (step 702—installation of sample).

(3) A distribution of an amplitude ($A_1$) and a phase ($\Delta p_1$) including the background and the sample is obtained by means of the fringe scanning method (step 703—actual measurement).

(4) The change in the amplitude $\Delta A$ ($=A_1/A_0$) caused by the sample is calculated (step 704—calculation of $\Delta A$ image) from a distributed image of the amplitude obtained at the above described steps (1) and (3).

After performing above procedure, the obtained $\Delta A$ image is displayed at a display unit 28 (step 708).

Figure 3:
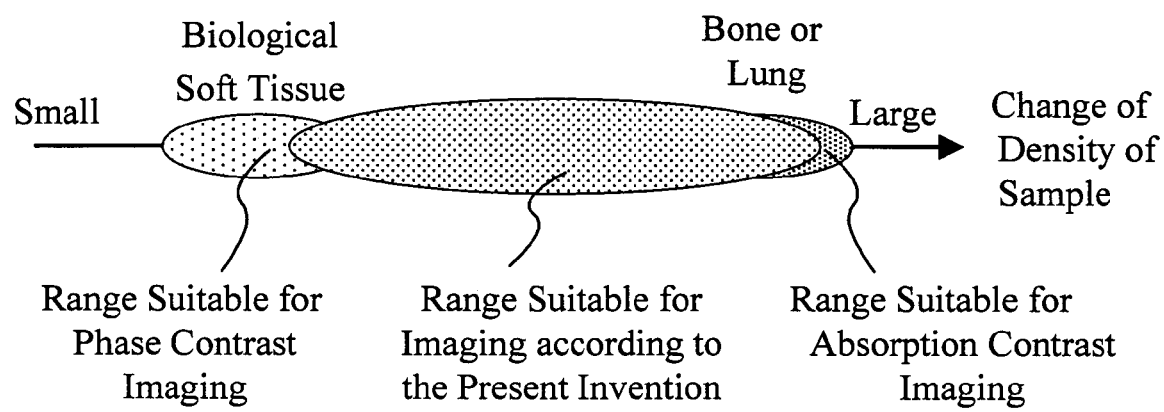
FIG. 3 is a view showing sensitivity ranges of conventional imaging methods and an imaging method according to the present invention.
Figure 4:
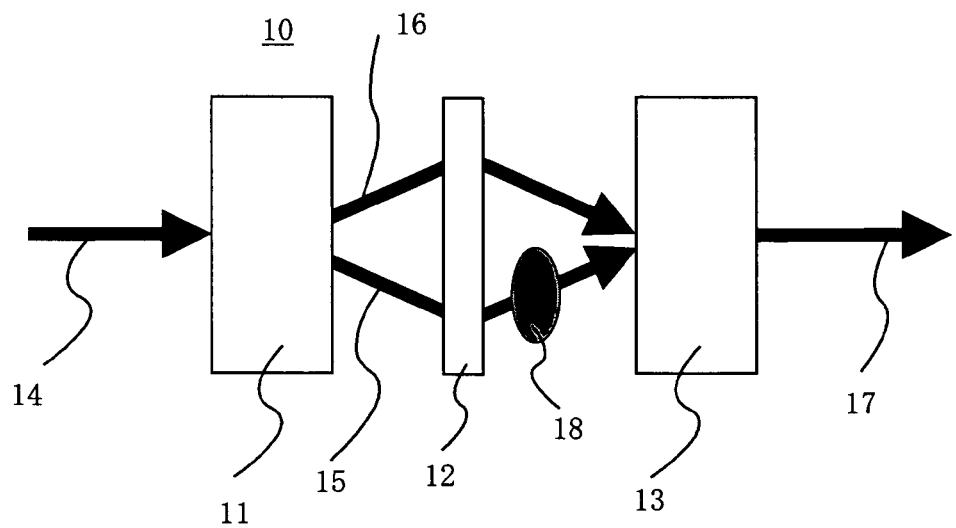
FIG. 4 is a schematic view showing a configuration of an X-ray interferometer.
Figure 5:
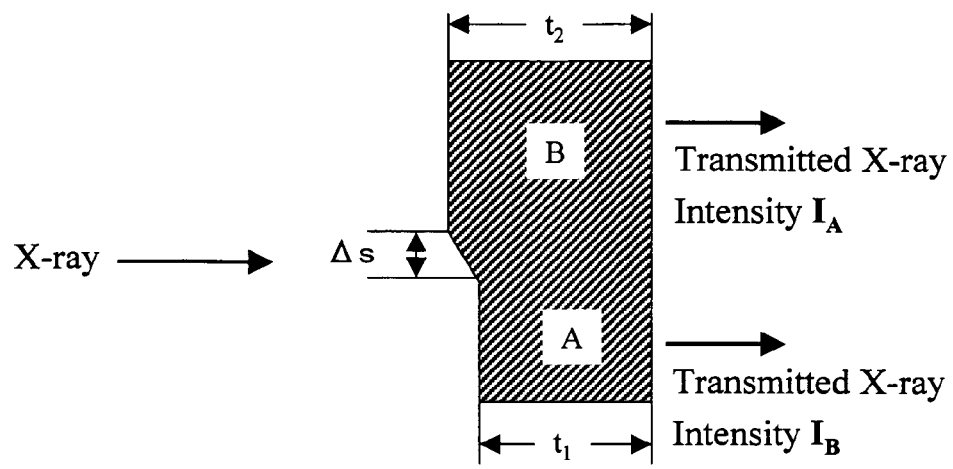
FIG. 5 is a view showing a cross sectional shape of a sample.

As mentioned before, a phase-shift $\Delta p$ can simultaneously be measured by the fringe scanning method and Fourier transformation method. Accordingly, by combining $\Delta A/A$ and $\Delta p$, all of the sensitivity range can be covered as shown in FIG. 3.

Figure 8:
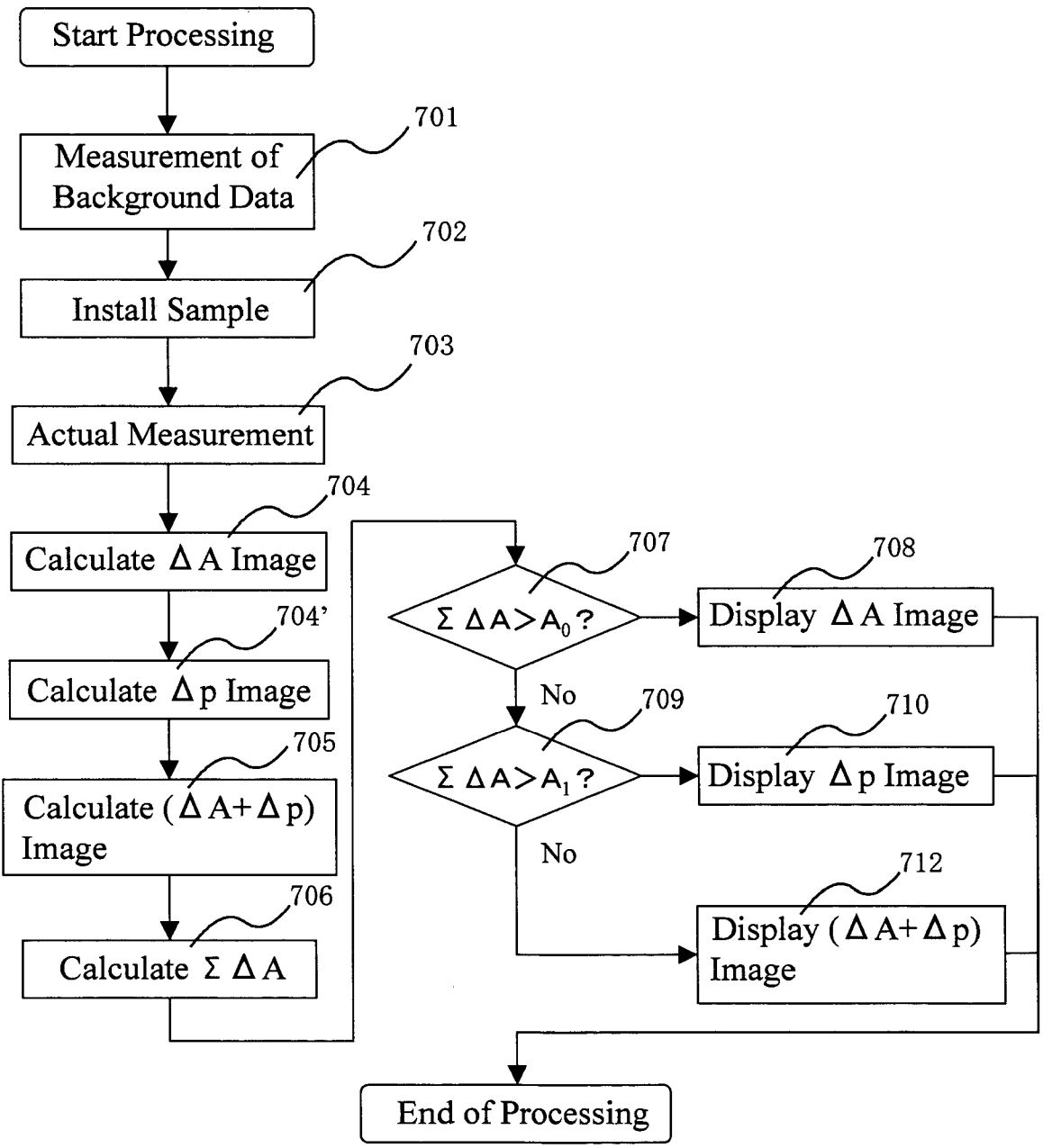
FIG. 8 is a view showing a procedure of another measurement according to the embodiment 1 of the present invention.

Following the processing in FIG. 7, in FIG. 8, (5) From the distribution image of the phase-shift obtained by the above described steps (1) and (3), the phase-shift $\Delta p$ ($=\Delta p_1 - \Delta p_0$) caused by the sample is calculated (step 704'—calculation of $\Delta p$ image) with conventional unwrapping processing.

Figure 9:
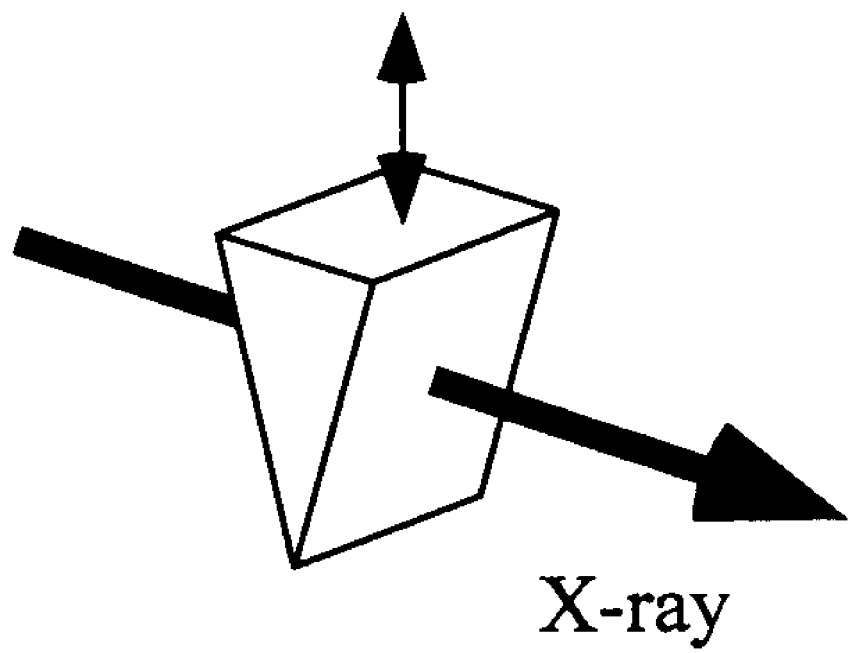
FIG. 9 is a view showing an example of a wedge type phase shifter.
Figure 10:
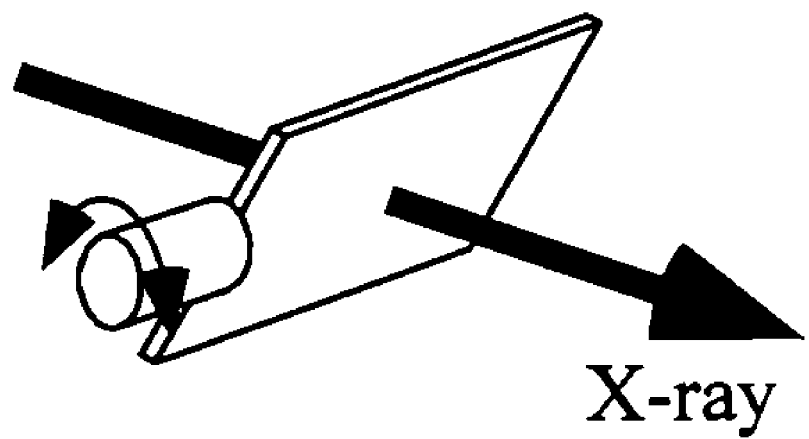
FIG. 10 is a view showing an example of a flat plate type phase shifter.

Incidentally, the fringe scanning method is performed by changing the phase of interfering beams. The phase is shifted by rotating or moving the phase shifter 23 in parallel with respect to the X-ray by using the phase shifter positioning mechanism 24. The changes in the amplitude and the phase are calculated from the obtained interference images at each phase-shift. In case of M sheets of the interference images whose phases are shifted at equal intervals, the amplitude A is given by an Equation (17).

$$A = \text{Abs}\left[\sum_{m=0}^{M-1} I_m \exp\left(-2\pi i \frac{m}{M}\right)\right] \quad (17)$$

where $I_m$ is an interference image with phase difference $2\pi m/M$. In addition, a phase shift $\Delta p$ is given by an Equation (18).

$$\Delta p = \text{Arg}\left[\sum_{m=0}^{M-1} I_m \exp\left(-2\pi i \frac{m}{M}\right)\right] \quad (18)$$

where a symbol Arg represents a calculation of argument. A generated phase shift amount by the phase shifter 23 can be selected either an unequal interval or an equal interval. Phase-shift can be generated by taking a wedge shaped acrylic plate as shown in FIG. 9 in and out to the optical path by the phase shifter positioning mechanism 24, or by rotating a flat shaped acrylic plate in the optical path by the phase shifter positioning mechanism 24. These operations are performed by the controller 26.

At the processing portion 27 shown in FIG. 6, (6) The combined image of the change in the amplitude and the phase is calculated (step 705—calculation of ($\Delta A + \Delta p$) image) from the images obtained by the above described steps, and held in the processing portion 27. The composition ratio of the changes in the amplitude and the phase is given by a ratio of the change in the amplitude $\Delta A$ and the maximum value $\Delta A_{max}$ of $\Delta A$. Namely, a composite value g is calculated by an Equation (19).

$$g = \frac{\Delta A}{\Delta A_{max}} \Delta p + \left(1 - \frac{\Delta A}{A_{max}}\right) \cdot \Delta A \quad (19)$$

As mentioned above, the optimum imaging method is depending upon the density of the sample. Thus, (7) the amount of the density change in the sample such as a magnitude (an integrated amount ($\Sigma \Delta A$) for entire image) etc., are calculated (step 706—calculation of $\Sigma \Delta A$).

At the display portion 28, an image which has the highest sensitivity and has been capable of imaging accurately from the images (the image of the change in the amplitude $\Delta A$, the image of the change in the phase $\Delta p$, and the composed image of the changes in the amplitude and the phase) held in the processing portion 27, is displayed automatically according to the value of this $\Sigma \Delta A$. To put it more concretely, $\Sigma \Delta A$ and A0 are compared with each other at step 707, and if $\Sigma \Delta A$ is larger than A0, the image of $\Delta A$ is displayed (step 708). At step 709, $\Sigma \Delta A$ and $A_1$ are compared with each other, if $\Sigma \Delta A$ is larger than $A_1$, the image of $\Delta p$ is displayed (step 710). If $\Sigma \Delta A$ is smaller than both A0 and $A_1$, the image of ($\Delta A + \Delta p$) is displayed (step 712).

Determination at each step 707 and 709 can be omitted, and when the calculations of 704 and 705 are finished, all of the images are sequentially displayed and/or the user select images to be displayed.

Figure 11A:
FIG. 11A is a view showing an example of a result of imaging according to a phase contrast.
Figure 11C:
FIG. 11C is a view showing an example of a result of imaging of the present invention using a composition of a change in an amplitude ΔA and a phase-shift Δp according to the embodiment 1 of the present invention.
Figure 11B:
FIG. 11B is a view showing an example of a result of imaging of the present invention using a change in an amplitude ΔA according to the embodiment 1 of the present invention.

FIG. 11A through FIG. 11C are views showing example images of biological sample obtained by using the embodiment 1. FIG. 11A shows the $\Delta p$ image obtained at step 704' in FIG. 8. This example cannot accurately show the phase-shift caused by the sample because of an unwrapping processing error. FIG. 11B shows the $\Delta A$ image obtained at step 704 in FIG. 8. This example (obtained by the present invention) can observe the image accurately even for the sample which has been impossible to observe the image accurately for the phase contrast method. FIG. 11C shows the ($\Delta A + \Delta p$) image obtained at step 705 in FIG. 8. By combining the changes in the amplitude and the phase, it becomes possible to visualize not only the bone but also a structure inside the soft tissue by the image of one sheet, and an internal structure can further precisely be observed.

As evident from the above description, according to the embodiment 1, the image of the change in the amplitude, the change in the phase, and the composite value of the changes in the amplitude and the phase of the interference beam as the contrast can be obtained as well. Therefore, even a sample including an organ of large density change such as the bone or the lung and an organ of small density change such as biological soft tissue can be observed in a state of high sensitivity.

Second Embodiment

In the embodiment 1, the change in the amplitude and the phase of the interference beam caused by the sample has been detected by using the fringe scanning method. To perform this method, three sheets of the interference images which are in phase relationships different from each other are required at least. Because of its long measurement time, therefore it is difficult to apply this method to the dynamical observations. Accordingly, the embodiment using the Fourier transformation method in place of the fringe scanning method will be shown in this case. In the Fourier transformation method, the change in the amplitude and the phase can be obtained by one sheet of the interference image, therefore the measuring time can significantly be shortened. On the other hand, the spatial resolution is slightly lowered as compared with that of the fringe scanning method, because the spatial resolution is determined mainly by an interval of Moire-image interference fringes as described later.

The same X-ray imaging apparatus shown in FIG. 6 can be adopted for the observation using the Fourier transformation method. To perform the Fourier transformation method, the wedge shaped phase shifter 23 shown in FIG. 9 which made of material having small absorption for X-ray such as the acrylic plate, is placed in one optical path of the interfering beams. As a result, the Moire interference fringes are formed in the interference image in a direction perpendicular to an inclined direction of the phase shifter 23. The intensity distribution of the interference image can be expressed as an Equation (20).

$$I(x,y)=\alpha(x,y)+c(x,y)\exp(2\pi i f_0 x)+c^*(x,y)\exp(-2\pi i f_0 x) \quad (20)$$

where c(c, y) is expressed by an Equation (21), $$c(x, y) = \frac{1}{2}A(x, y)\exp(i\Delta p(x, y)) \quad (21)$$

where α is a background intensity distribution having no relation with an interference fringe, A is an amplitude of an interference fringe, Δp is a phase shift caused by the sample, f0 is a spatial frequency in an x direction of Moire interference fringes. Additionally, * indicates a complex conjugate. By the Fourier transformation calculation of Equation (20), frequency spectrum IF(x, y) in an x direction is given as an Equation (22).

$$I_F(f,y)=\alpha_F(f,y)+c_F(f-f_0,y)+c_F^*(f+f_0,y) \quad (22)$$

By setting the angle of the phase shifter 23 that the spacing of the Moire interference fringes is sufficiently narrowed as compared with a structure of the sample, αF, CF and CF* become completely separated spectra in the Equation (22). Therefore, by performing the inverse Fourier transformation of the CF or CF* component after shifted by f0 in a direction of the origin, only c including information of the change in the amplitude A and the phase of the interference fringe can be obtained. Therefore, the amplitude A can be obtained by a calculation of an absolute value of c, and the phase Δp can be obtained by a calculation of the angle of deviation.

The measurement can be performed by a procedure which is similar to that of the embodiment 1 (FIG. 8). The Fourier transformation method is used in place of the fringe scanning method for the measurement of the background data (step 701) and the actual measurement (step 703). The magnitude (integrated amount (ΣΔA) of the phase of the amplitude for entire image) etc. is also calculated in the same way as the embodiment 1. And according to this value, an image having best sensitivity and having been capable of imaging accurately is selected from the image of the measured change in the amplitude ΔA, the image of the measured change in the phase Δp, and the composed image of the change in the amplitude and the phase, and is displayed at the display unit 28. Or, all of the images are displayed so as to be selectable.

As evident from the above description, according to the embodiment 2, the image of the change in the amplitude, the change in the phase, and the composite value of the changes in the amplitude and the phase of the interference beam as the contrast can be obtained in a short time. Therefore, even a sample including a organ of large density change such as the bone or the lung and a organ of small density change such as biological soft tissue can be observed in a state of high sensitivity and high time resolution.

Third Embodiment

Figure 12:
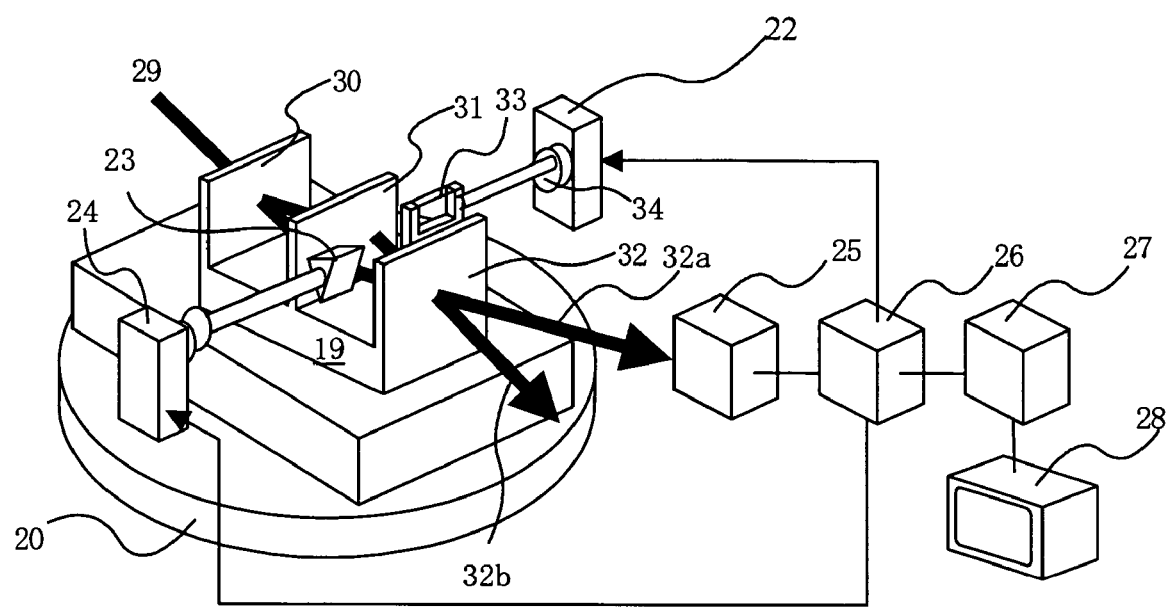
FIG. 12 is a view showing a configuration example of the embodiment 3 of an X-ray imaging apparatus capable of obtaining a sectional image nondestructively by utilizing a CT technique.

In the embodiments 1 and 2, only the image (transmitted image) passing through the sample can be measured. An embodiment capable of observing the inside of the sample nondestructively will be shown. FIG. 12 is a block diagram showing a constitution of the embodiment 3.

The apparatus is similar to that of the embodiments 1 and 2 excluding a sample holder 33 and a sample holder rotating mechanism 34. The sample is fixed to the sample holder 33, and rotated in a direction perpendicular to an optical axis by the sample holder rotating mechanism 34. In order to reduce an influence by the shape of the sample, the inside of the sample holder 33 may be filled up with a liquid having the density close to the density of the sample.

Figure 13:
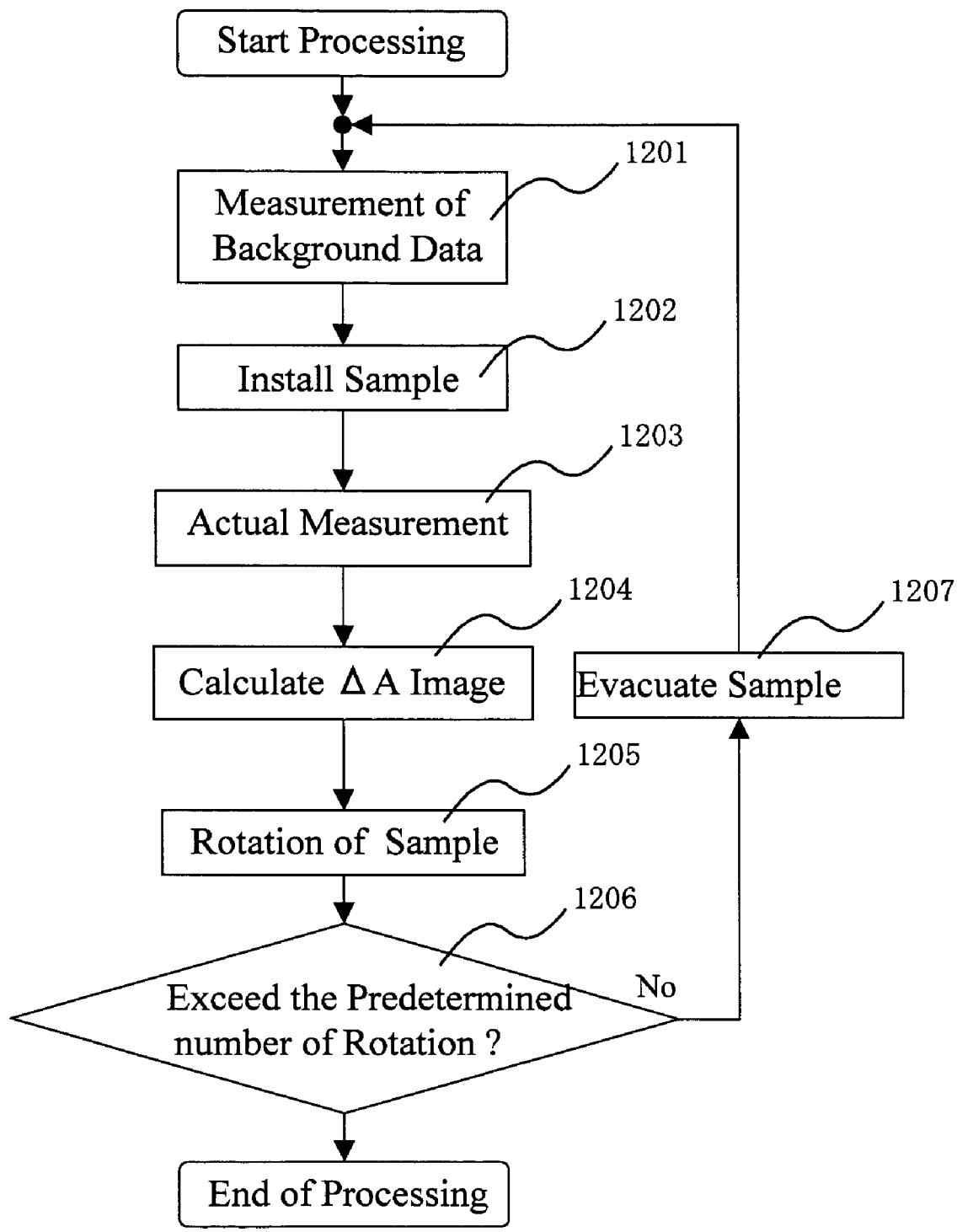
FIG. 13 is a view showing a procedure of measurement according to the embodiment 1 of the present invention in CT.

In the embodiment 3, the measurement is performed by the procedure shown in FIG. 13.

(1) Similar to the procedure of the first half of FIG. 7, the step 1201 (measurement of background data), the step 1202 (placing the sample in the optical path), and the step 1203 (actual measurement) is executed, and at the step 1204, the change in the amplitude ΔA caused by the sample is obtained.

(2) At step 1205, the sample is rotated by Δr by the sample rotating mechanism 34.

(3) At step 1206, it is determined whether the sample has finished the rotation at the predetermined number of rotation.

(4) When the sample has not finished the predetermined number of rotation, the sample is evacuated from the optical path at step 1207, then proceeds to step 1201 (measurement of background data), the measurement is repeated according to the similar procedures.

(5) The above procedures (1) through (4) are repeated the required number of steps n (=180°/Δr), and when above iteration reached the predetermined number of rotation, the measurement is terminated. After the measurement, a cross sectional image of the change in the amplitude ΔA as the contrast is reconstituted (step 1204 (calculation of ΔA image)) from the measured data set.

Figure 14:
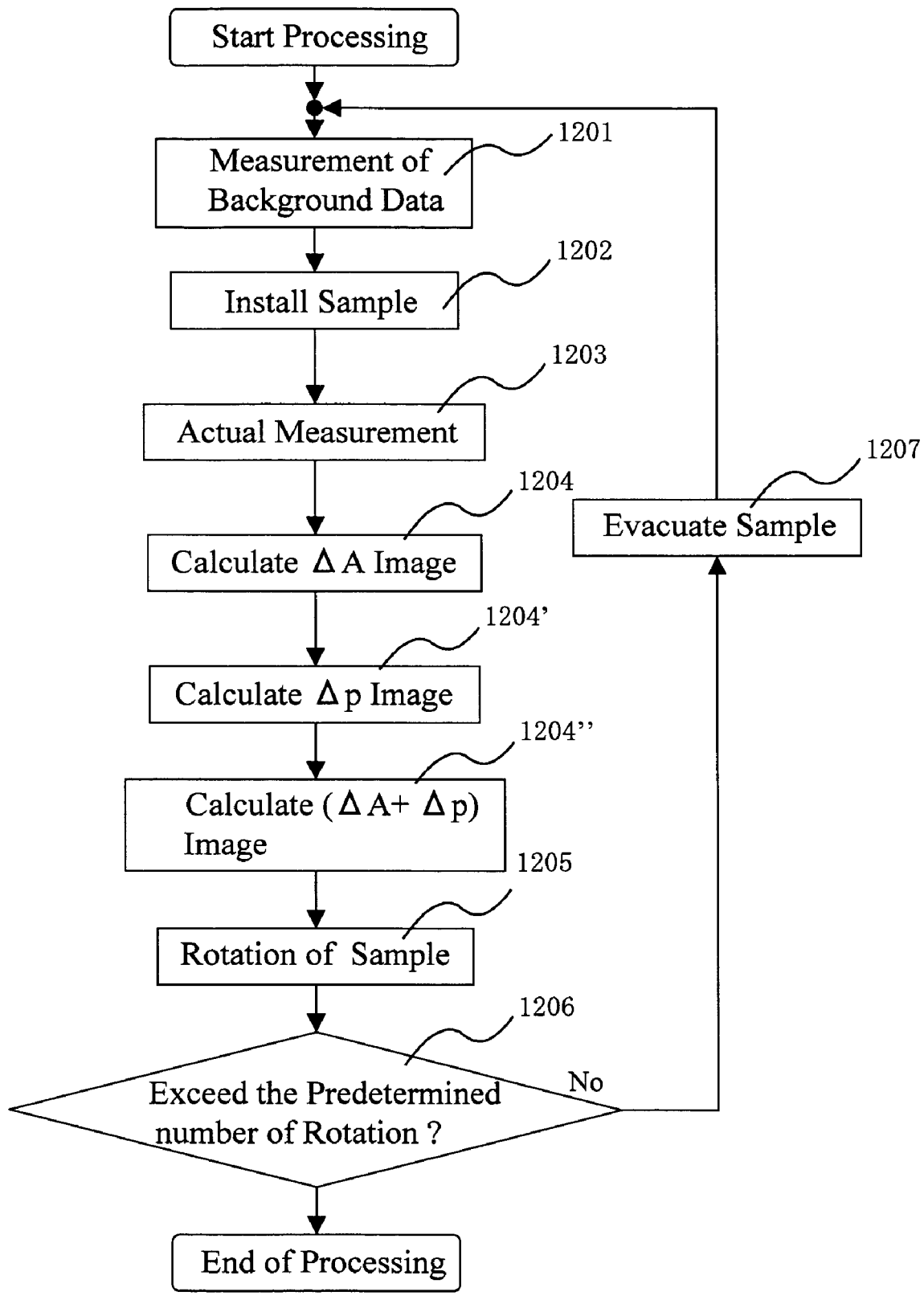
FIG. 14 is a view showing another procedure of measurement according to the embodiment 1 of the present invention in CT.

Similar to the embodiment 1, not only the change in the amplitude ΔA, but also the change in the phase Δp can simultaneously be measured at step 1203 (actual measurement). Thus, by utilizing these data, the image of the change in the amplitude, the change in the phase, and the composite value of the change in the amplitude and the phase can be obtained (step 1204' (calculation of Δp image) and step 1204" (calculation of (ΔA+Δp)image)) as shown in FIG. 14. Meanwhile, the composition of the amplitude A and Δp is carried out by a method similar to that of the embodiment 1.

The magnitude (integrated amount (ΣΔA) of the phase of the amplitude for entire image) etc. is calculated in the same way as the embodiment 1. And according to this value, an image having best sensitivity and having been capable of imaging accurately is selected from the image of the measured change in the amplitude ΔA, the image of the measured change in the phase Δp, and the composed image of the change in the amplitude and the phase, and is displayed at the display unit 28. Or, all of the images are displayed so as to be selectable.

As evident from the above description, according to the third embodiment 3, there can be provided the cross sectional image of the change in the amplitude, the change in the phase, and the composite value of the change in the amplitude and the phase as the contrast. Therefore, even a sample including an organ of large density change such as the bone or the lung and a organ of small density change such as biological soft tissue can be observed its internal structure nondestructively in a state of high sensitivity.

Fourth Embodiment

Figure 15:
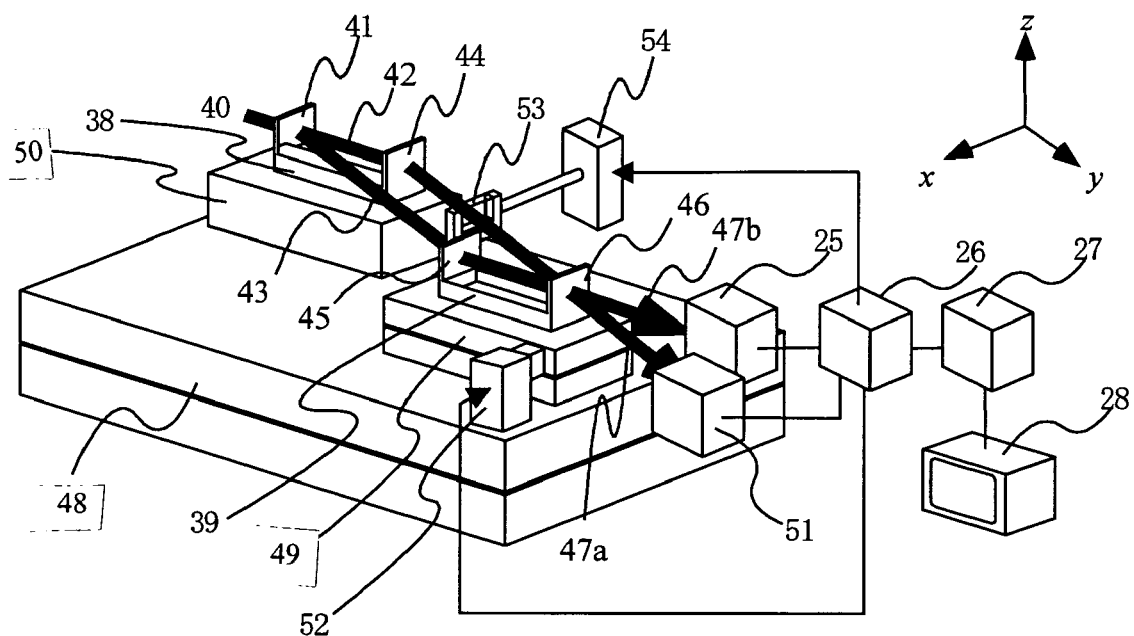
FIG. 15 is a view showing a configuration example of the embodiment 4 of an X-ray-imaging apparatus using a two-crystal X-ray interferometer.

Since the X-ray interferometer used in the embodiment 1 through 3 is constituted by one crystal block, the size of the interferometer is limited by a diameter of a crystal ingot. The field of view, therefore, could not widen 2 cm or more. As shown in FIG. 15, an example of the imaging apparatus having 2 cm or more field of view using two-crystal X-ray interferometer is given.

In the embodiment 4, in order to widen the field of view, a two-crystal X-ray interferometer constituted by a first crystal block 38 and a second crystal block 39 having two wafers as shown in FIG. 15 is used. An incident X-ray 40 is split into a first beam 42 and a second beam 43 by X-ray diffraction of a Laue case by a first wafer 41 of the first crystal block 38. The first beam 42 is diffracted by a second wafer 44 of the first crystal block 38 and the second beam 43 is diffracted by a third wafer 45 of the second crystal block 39. Both diffracted beams incident at the same point on a fourth wafer 46 of the second crystal block 39, and combined to form a first interference beam 47a and a second interference beam 47b.

The relative rotational fluctuation around Z axis between the first crystal block 38 and the second crystal block 39 causes the fluctuation of phase of the interference beam. Therefore, in order to perform stable imagines, above rotational fluctuation must be controlled with significantly good precision. A relationship between the fluctuation of mechanical rotation Δθ and the fluctuation of phase of interference beam Δϕ is given by an Equation (23).

$$\Delta\phi = \frac{2\pi\Delta\theta(x+t)}{d} \quad (23)$$

where t is a thickness of wafer of interferometer, x is an space between crystal wafers (between 41 and 44, 45 and 46), d is an Bragg-plane spacing, $\theta_B$ is a Bragg angle. For example, by utilizing diffraction of Si (220) (d=0.192 nm) under the condition of λ=0.07 nm, L=20 m, x=63 nm and $\theta_B$=10.5°, it is calculated from Equation (23) that Δθ=2 nrad corresponds Δϕ=2π approximately. Accordingly, in order to execute stable measurement, Δθ must be controlled at least by the precision of sub-n rad.

In order to realize the above described positioning precision, positioning between the crystal blocks is carried out by a stage group (constituted by a first θ table 48 used for the θ axis rotation of entire interferometer, a second θ table 49 used for the θ axis rotation of the second crystal 39 and a tilt table 50 used for the rotation of a ϕ axis of the first crystal 38) using a sleeve bearing mechanism with slipping sheets to enhance the mechanical rigidity in the embodiment 4. A positioning mechanism 52 having the extraordinary high precision using a piezoelectric device etc. is used for a second θ stage 49 which is required for the sub-nrad positioning. In addition, a feedback positioning mechanism controlling the rotation angle between the crystal blocks by a feedback loop is employed for the suppressing of a drift of Δθ for a long time. The feedback mechanism uses a detector 51 for detecting the intensity of the first interference beam 47a, and when the intensity of the first interference beam is fluctuated due to drift rotation of Δθ, the feedback mechanism adjusts the rotation of the second θ table 49 via the positioning mechanism 52 so as to cancel the fluctuation at once. Furthermore, in the case of that above described control mechanism cannot sufficiently suppress the drift of Δθ resulting from the fluctuation of the intensity of the incident X-ray, a two dimensional X-ray detector is suitable for the detector 51. The feedback control is performed by adjusting the rotation of the second θ table 49 so as to cancel the motion of position of the Moire interference fringes.

Each of a sample holder 53 and a sample holder positioning mechanism 54 has a function for rotating a sample similar to that of the embodiment 3. As a result, it is possible to observe the inside of the sample nondestructively by using the measurement similar to the embodiment 3.

The measurement is carried out similar to the embodiments 1 and 3. The magnitude (an integrated amount (ΣΔA) of the phase of the amplitude for entire image) etc. is calculated. According to this value, an image having best sensitivity and having been capable of imaging accurately is extracted from the images (the image of the change in the amplitude ΔA, the image of the change in the phase Δp, and the composed image of the change in the amplitude and the phase) held at the processing portion 27 and is displayed at the display unit 28.

As evident from the above description, according to the fourth embodiment 4, even the size of a sample is more than 2 cm, there can be obtained the transmission image and the cross sectional image of the change in the amplitude, the change in the phase, and the composite value of the change in the amplitude and the phase of the interference beam as the contrast. Even a sample in which a portion having a large change in density and a portion having a small change in density are mixed, the sample can be observed in a state of high sensitivity.

According to the present invention, the imaging apparatus and imaging method using the amount of change in the amplitude caused by the sample as the contrast and/or the amount composed of the amount of change in the amplitude and the amount of phase-shift caused by the sample as the contrast, enables to observe a sample including a organ of large density change such as the bone or the lung and a organ of small density change such as biological soft tissue, which has heretofore been difficult by means of the conventional adsorption and the phase contrast X-ray imaging apparatuses, in a state of high-sensitivity.

Reference numerals in drawings are as follows:

1: beam splitter, 2: mirror, 3: analyzer, 4: X-ray, 5 and 6: beam, 7 and 8: interference beams, 9: sample, 10: X-ray interferometer, 11: splitter, 12: mirror optical system, 13: analyzer, 14: incident X-ray beam, 15: first beam, 16: second beam, 17: interference beam, 18: sample, 19: X-ray interferometer, 20: position adjusting mechanism, 21: sample holder, 22: sample holder positioning mechanism, 23: phase shifter, 24: phase shifter positioning mechanism, 25: X-ray detector, 26: controller, 27: processing portion, 28: display unit, 29: incident X-ray, 30: splitter, 31: mirror, 32: analyzer, 32a: first interference beam, 32b: second interference beam, 33: sample holder, 34: sample holder rotating mechanism, 38: first crystal block, 39: second crystal block, 40: incident X-ray, 41: fist wafer, 42: first beam, 43: second beam, 44: second wafer, 45: third wafer, 46: fourth wafer, 47a: first interference beam, 47b: second interference beam, 48: first θ table, 49: second θ table, 50: tilt table, 51: detector, 52: positioning mechanism, 53: sample holder, 54: sample holder positioning mechanism.

What is claimed is:

1. An X-ray imaging apparatus, comprising:
   an X-ray interferometer constituted by a splitting device for splitting an incident X-ray beam into a first X-ray beam and a second X-ray beam, a reflecting device for reflecting said first X-ray beam and said second X-ray beam, and a combining device for combining a first reflected X-ray beam and a second reflected X-ray beam,
   means for placing a sample in an optical path of an arbitrary beam of said first and second X-ray beams,
   means for placing a phase shifter in an optical path of an arbitrary beam of said first and second X-ray beams,
   a detector for detecting an interference X-ray beam emitted from said X-ray interferometer; and
   a processing portion for obtaining an image of said sample based on an output of said detector,
   wherein said processing portion generates an image based on a change of an interference amplitude caused by said sample, which is represented by an equation $2r'\sqrt{(I_1+\Delta I)\cdot I_2}$, and the equation is a part of an equation representing intensity I' of the interference X-ray beam $I'=(I_1-\Delta I)+I_2+2r'\sqrt{(I_1-\Delta I)\cdot I_2}\cdot\cos(\phi+\Delta p)$ where $I_1$ represents the intensity of one of said first and second X-ray beams in the optical path of which said sample is placed, $I_2$ represents the intensity of the other of said first and second X-ray beams, $\Delta I$ represents the change in the intensity of one of said first and second X-ray beams in the optical path of which said sample is placed, r' represents a changed degree of coherence according to a change in the direction of an X-ray caused by said sample placed in an optical path of one of said first and second X-ray beams, φ represents a phase difference between said first and second X-ray beams, and Δp represents phase-shift caused by the sample placed in an optical path of one of said first and second X-ray beams.

2. An X-ray imaging apparatus as set forth in claim 1, further comprising means for reproducing a cross sectional image of said sample from a plurality of sample images obtained by rotating said sample in a direction perpendicular to the optical path of an X-ray beam.

3. An X-ray imaging apparatus as set forth in claim 1, wherein said X-ray interferometer is a single crystal block comprising a plurality of sheets of crystal wafers formed monolithically with a groundsill holding these wafers.

4. An X-ray imaging apparatus as set forth in claim 1, wherein said X-ray interferometer comprises a combination of crystal blocks comprising a plurality of sheets of crystal wafers formed monolithically with a groundsill holding these wafers.

5. An X-ray imaging apparatus as set forth in claim 1, wherein a shape of said phase shifter is a wedge type.

6. An X-ray imaging apparatus, comprising:
   an X-ray interferometer constituted by a splitting device for splitting an incident X-ray beam into a first X-ray beam and a second X-ray beam, a reflecting device for reflecting said first X-ray beam and said second X-ray beam, and a combining device for combining a first reflected X-ray beam and a second reflected X-ray beam,
   means for placing a sample in an optical path of an arbitrary beam of said first and second X-ray beams,
   means for placing a phase shifter in an optical path of an arbitrary beam of said first and second X-ray beams,
   a detector for detecting an interference X-ray beam emitted from said X-ray interferometer; and
   a processing portion for obtaining an image of said sample based on an output of said detector,
   wherein said processing portion generates an image based on a change of an interference amplitude $2r'\sqrt{(I_1-\Delta I)\cdot I_2}$, which is caused by said sample, and a phase-shift Δp, which is caused by said sample placed in an optical path of one of said first and second X-ray beams, wherein said change of an interference amplitude and the phase-shift are parts of an equation representing intensity I' of the intereference X-ray beam $I'=(I_1-\Delta I)+I_2+2r'\sqrt{(I_1-\Delta I)\cdot I_2}\cdot\cos(\phi+\Delta p)$ where $I_1$ represents the intensity of one of said first and second X-ray beams in the optical path of which said sample is placed, $I_2$ represents the intensity of the other of said first and second X-ray beams, $\Delta I$ represents the change in the intensity of one of said first and second X-ray beams in the optical path of which said sample is placed, r' represents a changed degree of coherence according to a change in the direction of an X-ray caused by said sample placed in an optical path of one of said first and second X-ray beams, and φ represents a phase difference between said first and second X-ray beams.

7. An X-ray imaging apparatus as set forth in claim 6, further comprising means for reproducing a cross sectional image of said sample from a plurality of sample images obtained by rotating said sample in a direction perpendicular to the optical path of an X-ray beam.

8. An X-ray imaging apparatus as set forth in claim 6, wherein said X-ray interferometer is a single crystal block comprising a plurality of sheets of crystal wafers formed monolithically with a groundsill holding these wafers.

9. An X-ray imaging apparatus as set forth in claim 6, wherein said X-ray interferometer comprises a combination of crystal blocks comprising a plurality of sheets of crystal wafers formed monolithically with a groundsill holding these wafers.

10. An X-ray imaging apparatus as set forth in claim 6, wherein a shape of said phase shifter is a wedge type.

11. An X-ray imaging method for splitting an incident X-ray beam into a first interfering beam and second interfering beam, comprising: placing a sample in an optical path of said first interfering beam, combining the first interfering beam and the second interfering beam, and obtaining an image of said sample from an interference X-ray beam formed by said combining, wherein the image of said sample is generated based on a change of an interference amplitude caused by said sample, which is represented by an equation $2r'\sqrt{(I_1-\Delta I) \cdot I_2}$, and the equation is a part of an equation representing intensity $I'$ of the interference beam $I'=(I_1-\Delta I)+I_2+2r'\sqrt{(I_1-\Delta I) \cdot I_2} \cdot \cos(\phi+\Delta p)$ where $I_1$ represents the intensity of one of said first and second interfering beams in the optical path of which said sample is placed, $I_2$ represents the intensity of the other of said first and second interfering beams, $\Delta I$ represents the change in the intensity of one of said first and second interfering beams in the optical path of which said sample is placed, $r'$ represents a changed degree of coherence according to a change in the direction of an interfering beam caused by said sample placed in an optical path of one of said first and second interfering beams, $\phi$ represents a phase difference between said first and second interfering beams, and $\Delta p$ represents phase-shift caused by the sample placed in an optical path of one of said first and second interfering beams.

12. An X-ray imaging method as set forth in claim 11, wherein a cross sectional image of said sample is reproduced from a plurality of sample images obtained by rotating said sample in a direction perpendicular to the optical path of said first interfering beam.

13. An X-ray imaging method as set forth in claim 11, further comprising the steps of:

placing a phase shifter in the optical path of the first interfering beam or the second interfering beam;

shifting a phase of the first interfering beam or the second interfering beam by relatively moving or rotating said phase shifter with respect to said optical path and obtaining an interference X-ray beam at different phase shifts; and finding the amount of change in the interference amplitude and an amount of change in a phase caused by said sample using a plurality of interference X-ray beams obtained by said shifting.

14. An X-ray imaging apparatus, comprising:

an X-ray interferometer constituted by a splitting device for splitting an incident X-ray beam into a first X-ray beam and a second X-ray beam, a reflecting device for reflecting said first X-ray beam and said second split X-ray beam, and a combining device for combining a first reflected X-ray beam and a second reflected X-ray beam, means for placing a sample in an optical path of an arbitrary beam of said first and second X-ray beams, means for placing a phase shifter in an optical path of an arbitrary beam of said first and second X-ray beams, a detector for detecting an interference X-ray beam emitted from said X-ray interferometer; and a processing portion for obtaining an image of said sample by combining an amount of change in an amplitude and an amount of change in a phase of the interference X-ray beam caused by said sample from an output of said detector, wherein combining of an amount of change in an amplitude and an amount of change in a phase of the interference X-ray beam performed in said processing portion is carried out by using a compositional ratio calculated from magnitude of an amount of change in an amplitude.

15. An X-ray imaging method for splitting an incident X-ray beam into a first interfering beam and a second interfering beam, placing a sample in an optical path of said first interfering beam, combining the first interfering beam and the second interfering beam, and obtaining an image of said sample from an interference X-ray beam formed by said combining, wherein the image of said sample is formed by using an amount of change in an amplitude of said interference X-ray beam caused by said sample, wherein the image of said sample is formed by using an amount composed of an amount of change in an amplitude and an amount of change in a phase of said interference X-ray beam caused by said sample; and wherein the composition of the amount of the change in the amplitude and the amount of the change in the phase is carried out by using a compositional ratio calculated based on magnitude of an amount of change in an amplitude.

16. An X-ray imaging method as set forth in claim 15, wherein a cross sectional image of said sample is reproduced from a plurality of sample images obtained by rotating said sample in a direction perpendicular to the optical path of said first interfering beam.

17. An X-ray imaging method as set forth in claim 15, further comprising the steps of:

placing a phase shifter in the optical path of the first interfering beam or the second interfering beam;

shifting a phase of the first interfering beam or the second interfering beam by relatively moving or rotating said phase shifter with respect to said optical path and obtaining an interference X-ray beam at different phase shifts; and finding the amount of change in the interference amplitude and an amount of change in a phase caused by said sample using a plurality of interference X-ray beams obtained by said shifting.

18. An X-ray imaging method for splitting an incident X-ray beam into a first interfering beam and a second interfering beam, placing a sample in an optical path of said first interfering beam, combining the first interfering beam and the second interfering beam, and obtaining an image of said sample from an interference X-ray beam formed by said combining, wherein the image of said sample is formed by using an amount of change in an amplitude of said interference X-ray beam caused by said sample, and further comprising the steps of:

placing a wedge type phase shifter in the optical path of the first interfering beam or the second interfering beam;

obtaining the interference beam;

Fourier transforming said interference X-ray beam;

shifting an obtained Fourier spectrum in a direction to an origin by a number of frequencies corresponding to an interval of Moire-image interferences fringes appearing in the interference X-ray beam;

inverse Fourier transforming the shifted spectrum; and finding the amount of change in an amplitude and an amount of change in a phase of said interference X-ray beam caused by said sample based on obtained data.

19. An X-ray imaging method for splitting an incident X-ray beam into a first interfering beam and a second interfering beam, placing a sample in an optical path of said first interfering beam, combining the first interfering beam and the second interfering beam, and obtaining an image of said sample from an interference X-ray beam formed by said combining, wherein the image of said sample is formed by using an amount of change in an amplitude of said interference X-ray beam caused by said sample, wherein the image of said sample is formed by using an amount composed of an amount of change in an amplitude and an amount of change in a phase of said interference X-ray beam caused by said sample, and further comprising the steps of:

placing a wedge type phase shifter in the optical path of the first interfering beam and the second interfering beam;

obtaining the interference beam;

Fourier transforming said interference X-ray beam;

shifting an obtained Fourier spectrum in a direction to an origin by a number of frequencies corresponding to an interval of Moire-image interference fringes appearing in the interference X-ray beam;

inverse Fourier transforming the shifted spectrum; and finding the amount of change in the amplitude and the amount of change in the phase of said interference X-ray beam caused by said sample based on obtained data.

* * * * *